(12) United States Patent
Lee et al.

(10) Patent No.: US 10,327,629 B2
(45) Date of Patent: Jun. 25, 2019

(54) ORAL DILATOR

(71) Applicants: MEGAFORCE COMPANY LIMITED, New Taipei (TW); MacKay Memorial Hospital, Taipei (TW)

(72) Inventors: Pei-Yi Lee, Taipei (TW); Shu-Fen Chen, Taipei (TW); Tien-Fu Chen, New Taipei (TW); Kai-Ping Wang, New Taipei (TW); Shunfeng Huang, New Taipei (TW); Yi-Shun Chung, New Taipei (TW); Shu-Hui Huang, New Taipei (TW); Yu-Siang Ji, New Taipei (TW); Zhen Wei Wu, New Taipei (TW)

(73) Assignees: MEGAFORCE COMPANY LIMITED, New Taipei (TW); MACKAY MEMORIAL HOSPITAL, Taipei (TW)

( * ) Notice: Subject to any disclaimer, the term of this patent is extended or adjusted under 35 U.S.C. 154(b) by 210 days.

(21) Appl. No.: 15/466,262

(22) Filed: Mar. 22, 2017

(65) Prior Publication Data
US 2018/0085274 A1   Mar. 29, 2018

(30) Foreign Application Priority Data

Sep. 23, 2016 (TW) .............................. 105214685 U
Nov. 27, 2016 (TW) .............................. 105218188 U

(51) Int. Cl.
*A61B 1/32* (2006.01)
*A61B 17/02* (2006.01)
*A61H 1/02* (2006.01)

(52) U.S. Cl.
CPC ................ *A61B 1/32* (2013.01); *A61B 17/02* (2013.01); *A61H 1/02* (2013.01); *A61H 2201/1436* (2013.01); *A61H 2201/5053* (2013.01); *A61H 2205/026* (2013.01)

(58) Field of Classification Search
CPC . A61B 17/02; A61B 17/0206; A61B 17/0218; A61B 17/025
USPC ................................. 600/237–239, 242, 244
See application file for complete search history.

(56) References Cited

U.S. PATENT DOCUMENTS

| | | | | |
|---|---|---|---|---|
| 606,781 | A * | 7/1898 | Halperin ................... | A61B 1/24 600/238 |
| 801,840 | A * | 10/1905 | Besant ..................... | A61B 1/24 600/238 |
| 1,137,585 | A * | 4/1915 | Craig, Jr. .................. | A61C 5/90 433/140 |
| 1,143,515 | A * | 6/1915 | Dunlop ..................... | A61B 1/24 433/139 |

(Continued)

*Primary Examiner* — Eric S Gibson
(74) *Attorney, Agent, or Firm* — Muncy, Geissler, Olds & Lowe, P.C.

(57) ABSTRACT

An oral dilator includes a first body, a second body, a rotary member, and a positioning member. The first body includes a housing and a first duckbilled element. The second body includes a second duckbilled element corresponding to the first duckbilled element. The rotary member drives the second body to rotate. The positioning member is on the first body and selectively locks or unlocks the relative position between the first duckbilled element and the second duckbilled element when the second duckbilled element is driven to rotate by the rotary member.

18 Claims, 10 Drawing Sheets

(56) References Cited

U.S. PATENT DOCUMENTS

| | | | | |
|---|---|---|---|---|
| 4,466,437 | A * | 8/1984 | Dyck | F16B 2/10 |
| | | | | 606/201 |
| 4,991,566 | A * | 2/1991 | Shulman | A61B 1/24 |
| | | | | 433/7 |
| 5,050,586 | A * | 9/1991 | Bonnell | A61B 17/24 |
| | | | | 433/42 |
| 5,097,820 | A * | 3/1992 | Shulman | A61B 1/24 |
| | | | | 600/237 |
| 6,168,601 | B1 * | 1/2001 | Martini | A61B 17/025 |
| | | | | 433/140 |
| 6,558,392 | B1 * | 5/2003 | Martini | A61B 17/025 |
| | | | | 433/140 |
| 6,805,127 | B1 * | 10/2004 | Karasic | A61M 16/0488 |
| | | | | 128/861 |
| 7,238,145 | B2 * | 7/2007 | Robbins | A63B 21/0004 |
| | | | | 482/11 |
| 7,607,917 | B2 * | 10/2009 | Virnicchi | A61B 1/00096 |
| | | | | 433/140 |
| 7,785,105 | B2 * | 8/2010 | Anderson | A61C 17/043 |
| | | | | 433/140 |
| 2003/0088158 | A1 * | 5/2003 | Chien | A63B 23/032 |
| | | | | 600/237 |
| 2008/0096165 | A1 * | 4/2008 | Virnicchi | A61B 1/00096 |
| | | | | 433/140 |
| 2016/0310234 | A1 * | 10/2016 | Ritter | A61B 1/24 |
| 2018/0085274 | A1 * | 3/2018 | Lee | A61H 1/02 |

\* cited by examiner

ORAL DILATOR

CROSS-REFERENCES TO RELATED APPLICATIONS

This non-provisional application claims priority under 35 U.S.C. § 119(a) to Patent Application No. 105214685 filed in Taiwan, R.O.C. on Sep. 23, 2016 and Patent Application No. 105218188 filed in Taiwan, R.O.C. on Nov. 28, 2016, the entire contents of which are hereby incorporated by reference.

BACKGROUND

Technical Field

The present invention relates to a medical rehabilitation tool, and in particular, to an oral dilator.

Related Art

After an operation or radiotherapy is performed on a patient that is ill in the head, the neck, or the oral cavity, fibrosis easily occurs to tissues of parts of chewing muscles or the jaw joints nearby the oral cavity, thereby causing problems such as gnathospasmus and difficulty in opening a mouth, which leads to a decreased life quality of a patient. For example, it is difficult for a patient to have food, so that nutrients are insufficient; and it is difficult for a patient to clean parts of the oral cavity, thereby leading to oral mucositis, periodontosis, and bacterial infection.

It is proved by clinical trials that, a problem of difficulty in opening a mouth caused by fibrosis of tissues can be avoided through rehabilitation of opening a mouth; and a probability of about 40% of incidence of oral mucositis can be reduced. In addition, rehabilitation can facilitate food taking, cleaning, and application of a drug, thereby avoiding infection.

The existing oral rehabilitation tool is generally to pile spatulas, and to force to increase a muscle extension force, to achieve an effect of opening a mouth, or to form a shape of a clamp by using spatulas, to perform oral dilation. Because such a rehabilitation tool is hard to be automatically operated by a patient, operating such a rehabilitation tool needs help from others, and it is hard to control a force, it is easy to cause a patient to be painful. Therefore, the patient does not want to perform rehabilitation.

SUMMARY

To resolve the problem in the prior art, this application provides an oral dilator that is suitable for a patient to perform an autonomous operation. The oral dilator includes a first body, a second body, a rotary member, and a positioning member. The first body includes a housing and a first duckbilled element. The second body includes a second duckbilled element corresponding to the first duckbilled element. The rotary member drives the second body to rotate. The positioning member is on the first body and selectively locks or unlocks the relative position between the first duckbilled element and the second duckbilled element when the second duckbilled element is driven to rotate by the rotary member.

In an embodiment, an oral dilator comprises a first body, a second body, a rotary member, and a positioning member. The first body comprises a housing and a first duckbilled element and the first duckbilled element is extended from the housing. The second body comprises a connecting portion and a second duckbilled element. The connecting portion is assembled with the housing. The second duckbilled element is extended from the connecting portion. The second duckbilled element is moved away from or toward the first duckbilled element for operating the oral dilator open or close. The rotary member comprises a central shaft and a gearwheel element. The gearwheel element includes a unidirectional gear row. The central shaft penetrates through the first body and the second body and connects to the gearwheel element. The rotary member drives to rotate the second body, and the second duckbilled element is moved for operating the oral dilator open or close. The positioning member is disposed on the first body and comprises a toggle block and a ratchet gear row. The toggle block controls an engagement of the ratchet gear row and the unidirectional gear row. The rotary member is only rotated along a single direction while the ratchet gear row engages with the unidirectional gear row.

In an embodiment, the housing includes a peripheral wall and an upper cover. The upper cover is above the second body, the rotary member, and the positioning member. The periphery wall is connected to the upper cover and forms an accommodation space therebetween. The peripheral wall is provided with an inserting groove which communicates to the accommodation space. The upper cover is provided with a first opening, the connecting portion is provided with a second opening, and the connecting portion of the second body is inserted to the inserting groove.

In an embodiment, the positioning member further includes a spring and a driving lever. The spring abuts against the ratchet gear row and an inner surface of the peripheral wall. The driving lever is extended out from a surface of the toggle block. When the driving lever is driven by power, the toggle block and the ratchet gear row are driven to move, and the spring is pressed, so that the unidirectional gear row is not in contact with the ratchet gear row. When the force on the driving lever is removed, an elastic force of the spring drives the toggle block and the ratchet gear row to be restored, so that the ratchet gear row engages with the unidirectional gear row. That is, when the driving lever is driven by power, the ratchet gear row gets away from the unidirectional gear row, so the gearwheel element can be freely rotate and not be limited. The second duckbilled element can be driven to move forward the first duckbilled element, such that the dilation angle between the first duckbilled element and the second duckbilled element can be reduced.

Further, the first body further includes a bottom cover. The bottom cover is fastened to at least one connection member extended from the lower surface of the upper cover, and seals the accommodation space. The bottom cover is provided with a sliding groove, and the driving lever passes through the sliding groove and protrudes above the bottom cover.

In an embodiment, the gearwheel element is provided with a third opening. The central shaft passes through the first opening, the second opening, and a third opening.

In an embodiment, the oral dilator further includes a fastening bolt, wherein the first opening of the first body is provided with a first groove, the second opening of the connecting portion is provided with a second groove, the third opening is provided with a third groove, the first groove, the second groove, and the third groove are in communication, the fastening bolt is fastened to the first groove, the second groove, and the third groove and abuts against the central shaft.

In an embodiment, the rotary member further includes a rotary switch. The rotary switch is located at an upper surface of the upper cover, and two ends of the central shaft are connected to the rotary switch and the gearwheel element, respectively.

In an embodiment, the toggle block includes a first through-hole, and the ratchet gear row includes a second through-hole. The toggle block is pivotally connected to the ratchet gear row by using a latch passing through the first through-hole and the second through-hole.

In an embodiment, the oral dilator further includes a snap ring. The snap ring is in contact with a surface of the gearwheel element, and the central shaft is sleeved by the snap ring.

In an embodiment, the inserting groove is engraved with multiple graduations, and the graduations correspond to intersection angles between the first duckbilled element and the second duckbilled element.

In an embodiment, an oral dilator comprises a first body, a second body, a rotary member, and a positioning member. The first body comprises a housing and a first duckbilled element. The housing comprises a peripheral wall and an upper cover. The upper cover is above the second body, the rotary member, and the positioning member. The periphery wall is connected to the upper cover and forms an accommodation space therebetween. The peripheral wall is provided with an inserting groove which communicates with the accommodation space. The upper cover is provided with a first opening and the first duckbilled element is extended from the housing. The second body comprises a connecting portion and a second duckbilled element. The connecting portion is inserted into the inserting groove. The connecting portion is provided with a second opening, and the second duckbilled element is extended from the connecting portion and corresponding to the first duckbilled element. The rotary member comprises a central shaft, a rotary switch and a rotary portion. The central shaft passes through the first opening and the second opening. The central shaft is connected to the rotary portion. The rotary portion is between the rotary switch and an upper surface of the upper cover. The rotary portion is provided with a first teeth portion. The rotary member is capable of being rotated to drive the second body to rotate. The positioning member comprises a second teeth portion disposed on a surface of the upper cover of the first body. The rotary member is locked when the second teeth portion engages with the first teeth portion.

In an embodiment, the oral dilator comprises a spring. The spring is located in the accommodation space. The central shaft is sleeved by the spring. The spring is in contact with a lower surface of the upper cover. The spring is not pressed when the first teeth portion engages with the second teeth portion. When the first teeth portion is moved away from the second teeth portion, an elastic force of the spring is formed to push the first teeth portion toward the second teeth portion.

In an embodiment, the oral dilator further comprises a fastening component. The fastening component is located in the accommodation space and sleeved by the spring. The fastening component fastens the central shaft.

In an embodiment, the first body further comprises a bottom cover. The bottom cover comprises a fastening groove to receive the fastening component. The bottom cover and the peripheral wall are connected to seal the accommodation space.

According to the oral dilator in the embodiments of this application, a structure of the oral dilator is ergonomic, so that a patient can operate the oral dilator without help from others. In addition, a positioning member of the oral dilator positions the opening angle between a first duckbilled element and a second duckbilled element. Accordingly, a dilation angle can be determined, thereby benefiting gradual mouth-opening rehabilitation and avoiding causing a painful feeling caused by excessive dilation. Moreover, rehabilitation situations can be observed and recorded, thereby encouraging the patient to use the oral dilator, avoiding fibrosis of chewing tissues, and improving food-taking and life quality of the patient.

DETAILED DESCRIPTION

Figure 1:
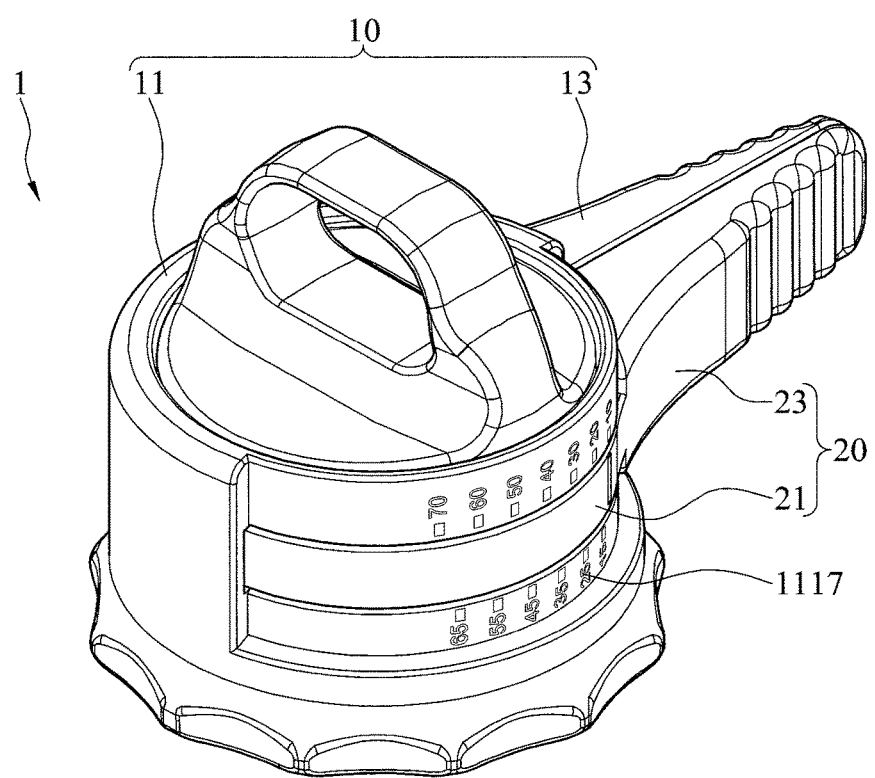
FIG. 1 illustrates a perspective view of the first embodiment of an oral dilator.
Figure 2A:
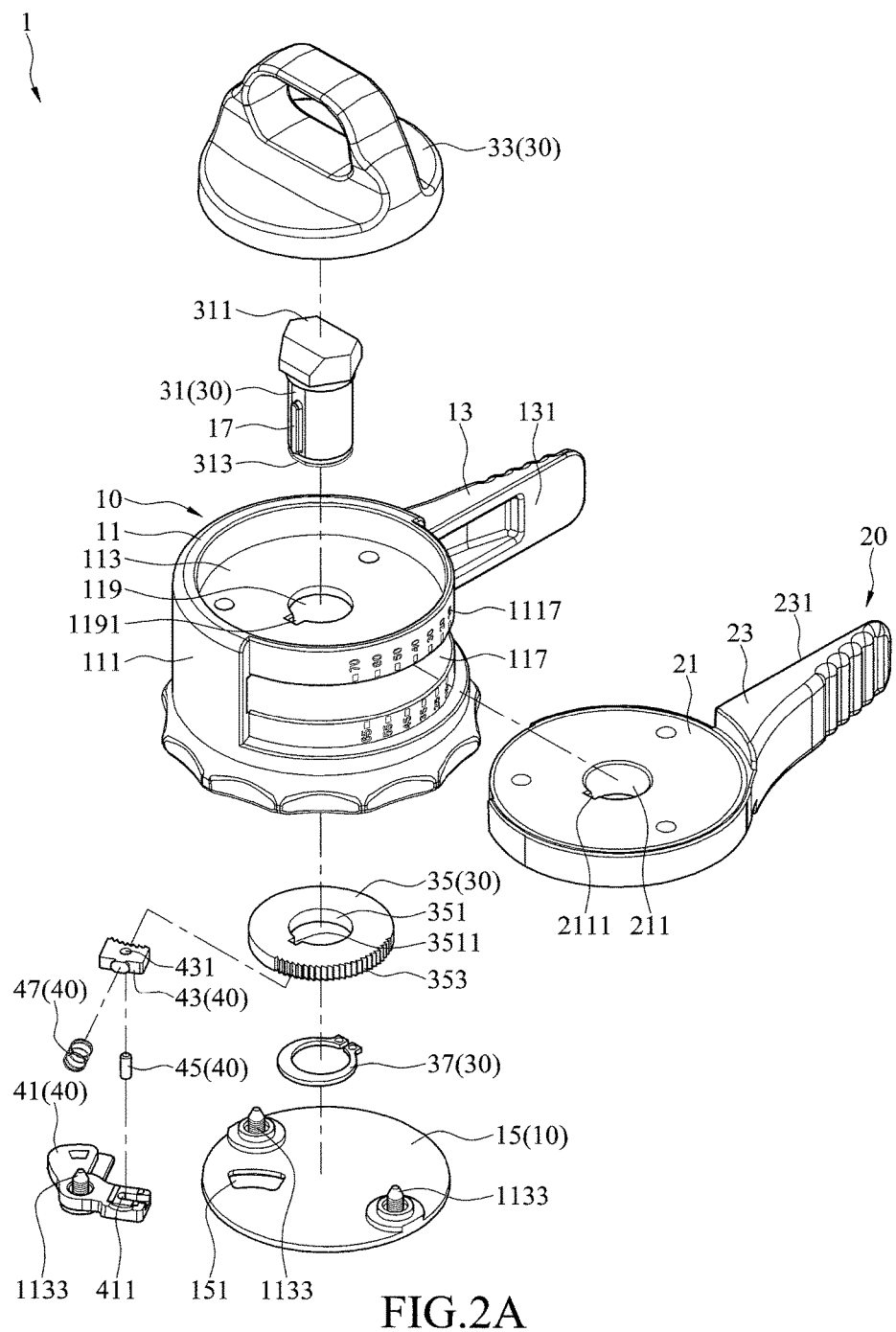
FIG. 2A illustrates an exploded view of the first embodiment of the oral dilator.
Figure 2B:
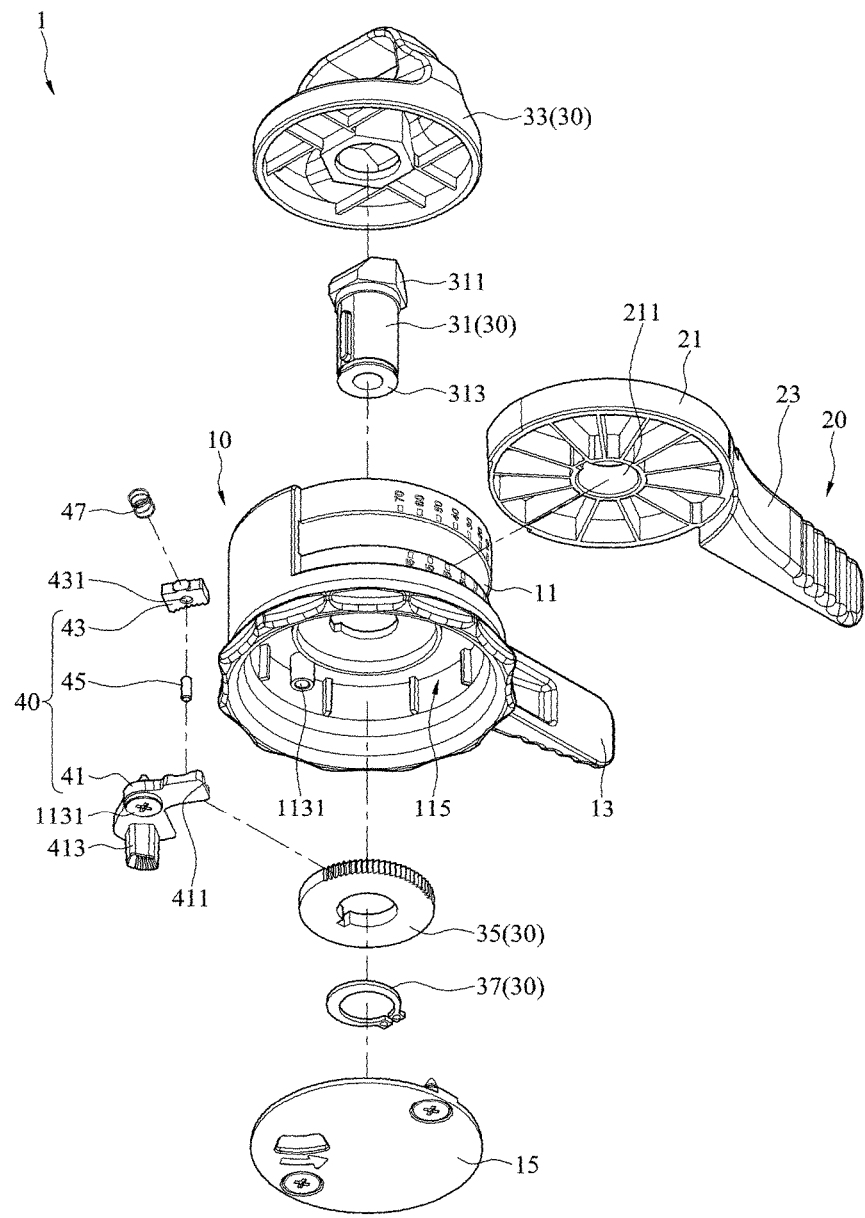
FIG. 2B illustrates another exploded view of the first embodiment of the oral dilator.

FIG. 1 illustrates a perspective view of the first embodiment of an oral dilator. FIG. 2A illustrates an exploded view of the first embodiment of the oral dilator. FIG. 2B illustrates another exploded view of the first embodiment of the oral dilator. As shown in FIG. 1, FIG. 2A, and FIG. 2B, the oral dilator 1 according to the first embodiment includes a first body 10, a second body 20, a rotary member 30, and a positioning member 40. The first body 10 includes a housing 11 and a first duckbilled element 13. The housing 11 includes a peripheral wall 111 and an upper cover 113. The upper cover 113 is above the second body 20, the rotary member 30, and the positioning member 40. The peripheral wall 111 is connected to the upper cover 113 to form an accommodation space 115. In this embodiment, the peripheral wall 111 of the housing 11 forms a cylindrical structure, which is merely used as an example but not a limitation to the present invention. The peripheral wall 111 is provided with an inserting groove 117. The inserting groove 117 is in communication with the accommodation space 115 inside the housing 11. In this embodiment, the inserting groove 117 is disposed from the centre of the peripheral wall 111. The upper cover 113 is provided with a first opening 119. The first duckbilled element 13 is extended out from the peripheral wall 111.

The second body 20 includes a connecting portion 21 and a second duckbilled element 23. The connecting portion 21 has a round-plate shape, but the connecting portion 21 is not limited thereto. The connecting portion 21 is inserted into the inserting groove 117, and the connecting portion 21 is provided with a second opening 211. The second duckbilled element 23 is extended out from the connecting portion 21 and corresponds to the first duckbilled element 13. The first duckbilled element 13 and the second duckbilled element 23 are in a mutually-reflected form in this embodiment. The first duckbilled element 13 includes a first touch surface 131. The second duckbilled element 23 includes a second touch surface 231. When the first duckbilled element 13 is in contact with the second duckbilled element 23, the first touch surface 131 and the second touch surface 231 contact each other.

The rotary member 30 includes a central shaft 31, a rotary switch 33, and a gearwheel element 35. In this embodiment, a first end 311 of the central shaft 31 cooperates with a rotary switch 33. For example, the first end 311 may be a projection buckling with a lower part of the rotary switch 33, or the first end 311 cooperates with the rotary switch 33 in a form of a screw, a rivet, a plug, a latch, or the like, which is merely an example but not a limitation to the present invention. Therefore, after the central shaft 31 is connected to the rotary switch 33, the central shaft 31 passes through the first opening 119 and the second opening 211. A lower surface of the rotary switch 33 is in contact with an upper surface of the upper cover 113. In this embodiment, the gearwheel element 35 is a unidirectional gear and located at another side of the rotary switch 33 relative to the central shaft 31. The gearwheel element 35 is provided with a third opening 351 and a unidirectional gear row 353. The central shaft 31 passes through the third opening 351 and is connected to the gearwheel element 35. Further, a second end 313 of the central shaft 31 may be sleeved and fastened by using a snap ring 37. The central shaft 31 is sleeved by the snap ring 37, and the snap ring 37 is in contact with the gearwheel element 35, to cause that the central shaft 31 can rotate but cannot move. Further, in the first embodiment, the first body 10, the second body 20, the rotary switch 33, and the gearwheel element 35 are disposed around the central shaft 31.

In this embodiment, the positioning member 40 includes a toggle block 41 and a ratchet gear row 43. The toggle block 41 is disposed inside the accommodation space 115 on the first body 10, and may be, by using a fastening member 1133, fastened to a lower surface of the upper cover 113 or the connection member 1131 extended from a lower surface of the upper cover 113. The fastening member 1133 may be a screw, a rivet, a fastening bolt, or the like; the connection member 1131 may be a shaft tube, a buckling first body, or the like, which are merely examples but not limitations thereto. The ratchet gear row 43 is connected to the toggle block 41. For example, the ratchet gear row 43 is pivotally connected to the toggle block 41 by using a latch 45; the latch 45 passes through a second through-hole 431 of the ratchet gear row 43 and is fastened to a first through-hole 411 of the toggle block 41, which is merely an example, but is not limited thereto. The ratchet gear row 43 and the unidirectional gear row 353 may engage with each other. When the ratchet gear row 43 engages the unidirectional gear row 353, rotation of the gearwheel element 35 is limited. That is, the gearwheel element 35 can only step-rotate along the unidirectional gear row 353 in one direction, and cannot rotate in a reverse direction. In this case, the second duckbilled element 23 is far away from the first duckbilled element 13, thereby enlarging an intersection angle between the second duckbilled element 23 and the first duckbilled element 13. The intersection angle is limited, so that the second duckbilled element 23 cannot be moved in a reverse direction, to reduce the intersection angle.

In addition, the first body 10 further includes a bottom cover 15. The bottom cover 15 is fastened to at least one connection member 1131 extended from the lower surface of the upper cover 113 by using the fastening member 1133, and seals the accommodation space 115. The bottom cover 15 bears the positioning member 40 and the gearwheel element 35. In this case, the connection member 1131 is a shaft tube, and the fastening member 1133 is a screw, which are merely examples but are not limitations thereto. The bottom cover 15 is further provided with a sliding groove 151. The driving lever 413 passes through the sliding groove 151 and protrudes above the bottom cover 15. That is, generally, during an operation, a user can operate the rotary switch 33 with one hand, and press the driving lever 413 with the other hand. The peripheral wall 111 is engraved with graduations 1117 at two sides of the inserting groove 117. The graduations 1117 correspond to rotated angles of the gearwheel element 35 and intersection angles between the second duckbilled element 23 and the first duckbilled element 13, to record rehabilitation cases.

Figure 3:
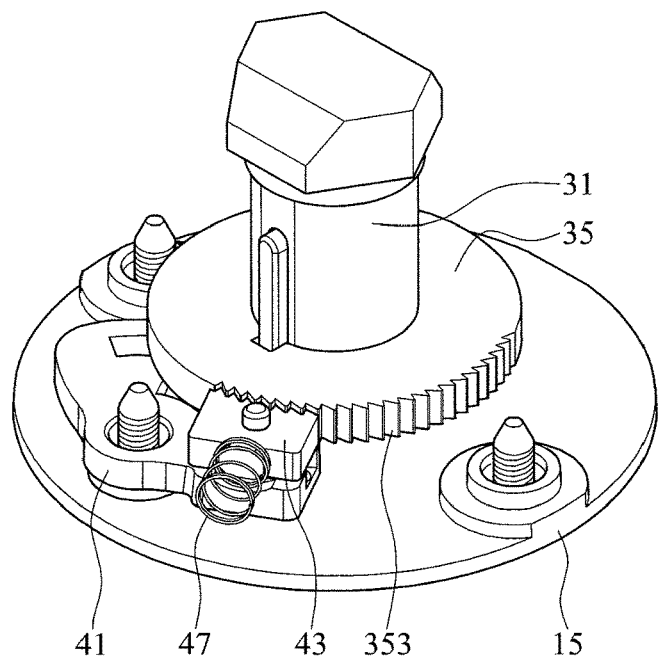
FIG. 3 illustrates a partial perspective view of the first embodiment of the oral dilator showing a positioning member at a lock state.
Figure 4:
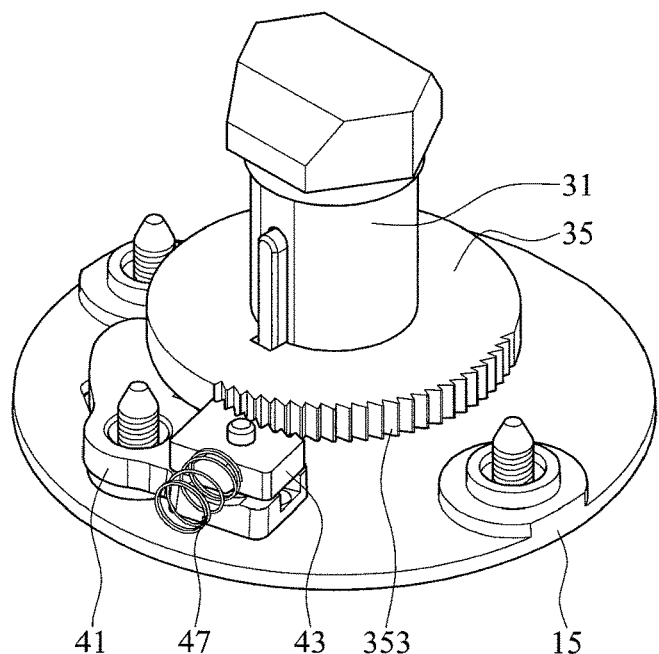
FIG. 4 illustrates another partial perspective view of a first embodiment of the oral dilator showing the positioning member at an unlock state.
Figure 5:
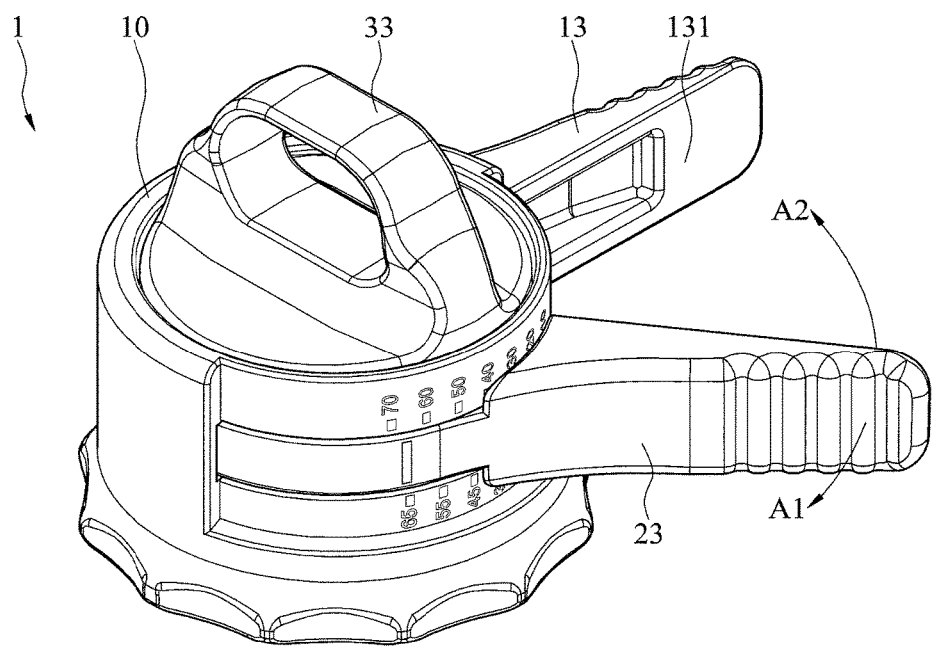
FIG. 5 illustrates another perspective view of the first embodiment of the oral dilator showing the dilator at an opening state.

FIG. 3 illustrates a partial perspective view of the first embodiment of the oral dilator showing a positioning member at a lock state. FIG. 4 illustrates another partial perspective view of a first embodiment of the oral dilator showing a positioning member at an unlock state. FIG. 5 illustrates another perspective view of the first embodiment of the oral dilator showing the dilator at an opening state. As shown in FIG. 3 and FIG. 4 and referring to FIG. 2, the positioning member 40 further includes a spring 47, and the toggle block 41 includes the driving lever 413. The spring 47 is configured to abut against the ratchet gear row 43 and an inner surface of the peripheral wall 111. The driving lever 413 is extended from a surface of the toggle block 41, to be a bearing rod. As shown in FIG. 3 and FIG. 5, when the unidirectional gear row 353 abuts against the ratchet gear row 43, rotation of the gearwheel element 35 is limited. Therefore, the unidirectional gear row 353 can only rotate in a particular direction and angle. In this case, as shown in FIG. 5, the gearwheel element 35 drives the second body 20 to rotate, so that the second duckbilled element 23 rotates along a first direction A1, and may rotate in a step manner by using the unidirectional gear row 353.

As shown in FIG. 4 and FIG. 5, when the driving lever 413 is driven by a force, the toggle block 41 and the ratchet gear row 43 are driven to move, and the spring 47 is pressed, so that the unidirectional gear row 353 gets away from the ratchet gear row 43, and the unidirectional gear row 353 and the ratchet gear row 43 do not contact each other. In this case, the gearwheel element 35 can be rotated at will, thereby driving the second body 20 to rotate in a reverse along direction A2, so that the second duckbilled element 23 moves towards the first duckbilled element 13. In this way, the intersection angle between the second duckbilled element 23 and the first duckbilled element 13 is reduced. When the force on the driving lever 413 is removed, an elastic force of the spring 45 drives the toggle block 41 and the ratchet gear row 43 to be restored, so that the ratchet gear row 43 engages with the unidirectional gear row 353 again, thereby restoring to a state in which rotation of the gearwheel element 35 is limited, which is shown in FIG. 3.

Further, referring to FIGS. 2A and 2B again, the oral dilator 1 further includes a fastening bolt 17. The first opening 119 of the first body 10 is provided with a first groove 1191. The second opening 211 of the connecting portion 21 is provided with a second groove 2111. The third opening 351 of the gearwheel element 35 is provided with a third groove 3511. The first groove 1191, the second groove 2111, and the third groove 3511 are in communication. The fastening bolt 17 is fastened to the first groove 1191, the second groove 2111, and the third groove 3511, and abuts against the central shaft 31, so that the central shaft 31 and the first body 10, the connecting portion 21, and the gearwheel element 35 are fastened together, thereby avoiding sliding.

Figure 6:
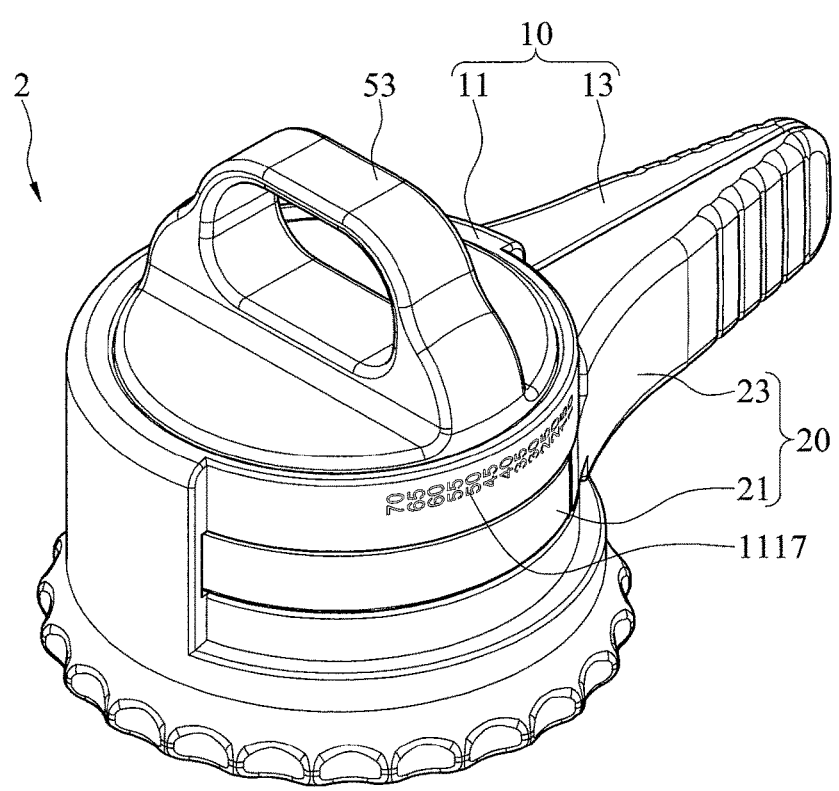
FIG. 6 illustrates a perspective view of the second embodiment of the oral dilator.
Figure 7A:
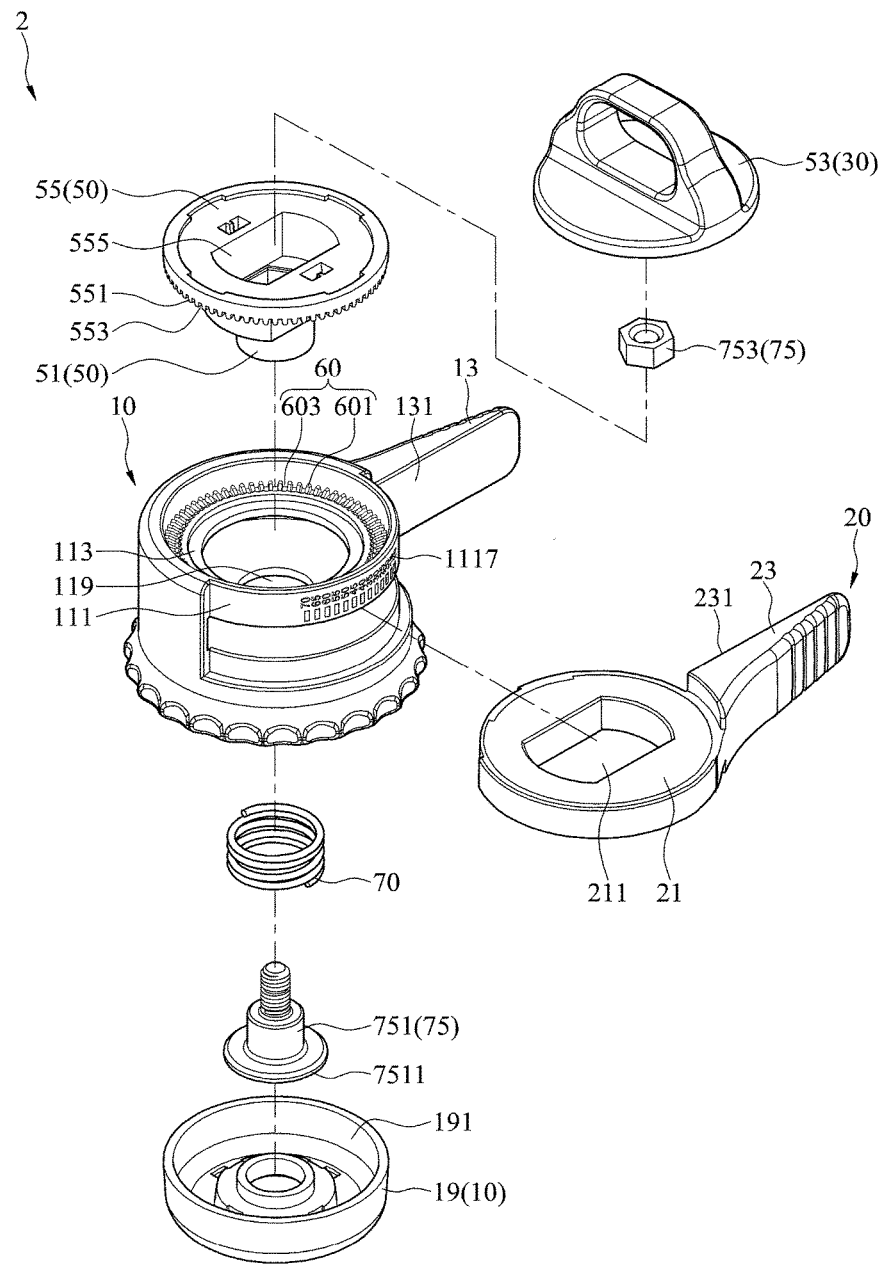
FIG. 7A illustrates an exploded view of a second embodiment of the oral dilator.
Figure 7B:
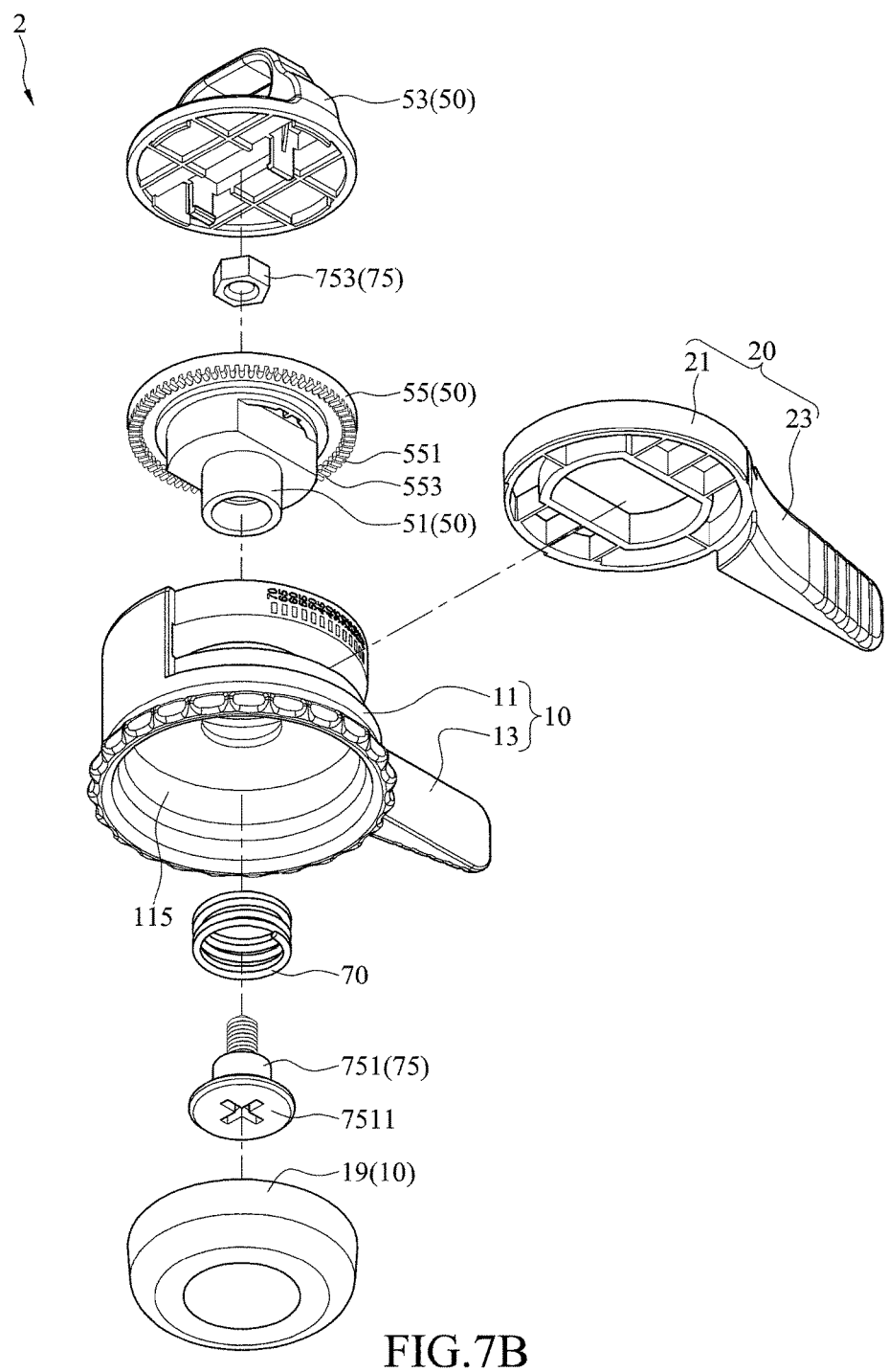
FIG. 7B illustrates another exploded view of the second embodiment of the oral dilator.

FIG. 6 illustrates perspective view of the second embodiment of the oral dilator. FIG. 7A illustrates an exploded view of a second embodiment of the oral dilator. FIG. 7B illustrates another exploded view of the second embodiment of the oral dilator. As shown in FIG. 6, FIG. 7A, and FIG. 7B, an oral dilator 2 according to the second embodiment includes a first body 10, a second body 20, a rotary member 50, and a positioning member 60. The first body 10 includes a housing 11 and a first duckbilled element 13. The housing 11 includes a peripheral wall 111 and an upper cover 113. The upper cover 113 is above the second body 20, the rotary member 50, and the positioning member 60. The peripheral wall 111 is connected to the upper cover 113 to form an accommodation space 115. The peripheral wall 111 of the housing 11 forms a cylindrical structure, which is merely an example but not a limitation thereto. The upper cover 113 is extended inside from the peripheral wall 111, and defines the first opening 119. The peripheral wall 111 is provided with an inserting groove 117. The inserting groove 117 is in communication with the accommodation space 115. The inserting groove 117 is disposed from the centre of the peripheral wall 111. The first duckbilled element 13 is extended out from the peripheral wall 111.

The second body 20 includes a connecting portion 21 and a second duckbilled element 23. The connecting portion 21 has a round-plate shape, but the connecting portion 21 is not limited thereto. The connecting portion 21 is inserted into the inserting groove 117. The connecting portion 21 is provided with a second opening 211. The second duckbilled element 23 is extended out from the connecting portion 21 and corresponds to the first duckbilled element 13. The first duckbilled element 13 and the second duckbilled element 23 are in a mutually-reflected form in this embodiment. The first duckbilled element 13 includes a first touch surface 131. The second duckbilled element 23 includes a second touch surface 231. When the first duckbilled element 13 is in contact with the second duckbilled element 23, the first touch surface 131 and the second touch surface 231 contact each other.

The rotary member 50 includes a central shaft 51, a rotary switch 53, and a rotary portion 55. In this embodiment, the rotary portion 55 and the central shaft 51 may be integrally formed. The rotary portion 55 is formed by extending in a loop at an outer surface of one end of the central shaft 51. That is, the rotary portion 55 and the central shaft 51 together form an umbrella-shaped or a mushroom-like shaped structure, which is merely an example but not a limitation thereto. The rotary portion 55 and the central shaft 51 may be separate parts. The rotary portion 55 is between the rotary switch 53 and an upper surface of the upper cover 113. The rotary portion 55 and the rotary switch 53 may buckle each other, for example, buckle each other by using corresponding projection and groove, or by using corresponding buckling hook and buckling groove. The above is merely an example, but not a limitation thereto. The central shaft 51 passes through the second opening 119 and the first opening 211.

In addition, there is a first teeth portion 551 on a lower surface of the rotary portion 55. The positioning member 60 has a second teeth portion 601 disposed on an upper surface of the upper cover 113. When crests of the first teeth portion 551 engage with the valleys 603 of the second teeth portion 601, and crests of the second teeth portion 601 engages with the valleys 553 of the first teeth portion 551, the first teeth portion 551 are blocked by the second teeth portion 601, thereby stopping the rotation of the rotary portion 55.

Further, the oral dilator 2 in the embodiment further includes a spring 70 and a fastening component 75. The spring 70 and the fastening component 75 are located within the accommodation space 115. The central shaft 51 is sleeved by the spring 70, and the spring 70 is in contact with a lower surface of the upper cover 113. A fastening component 75 is in contact with the spring 70, and the central shaft 55 is fastened by the fastening component 75. The central shaft 51 may have a hollow-tube shape. The fastening component 75 is a combination of the screw 751 and the nut 753. The nut 753 is located at a central groove area of the rotary member 55, and corresponds to the second opening 119 and the first opening 211, which is merely used as an example. The nut 753 may also be located at the upper surface of the upper cover 113. The screw 751 passes through the central shaft 51 and buckles with the nut 753. A diameter of the head 7511 of the screw 751 is greater than a diameter of the central shaft 51, thereby fastening the rotary member 50 and the second body 20. In addition, the first body 10 further includes a bottom cover 19. The bottom cover 19 includes a fastening groove 191, to accommodate the fastening component 75, especially, the cap-edge portion 7511 of the screw 751. The bottom cover 19 and the peripheral wall 111 work together, to seal the accommodation space 115. In addition, the spring 70 is in contact with the cap-edge portion 7511 of the screw 751.

Figure 8:
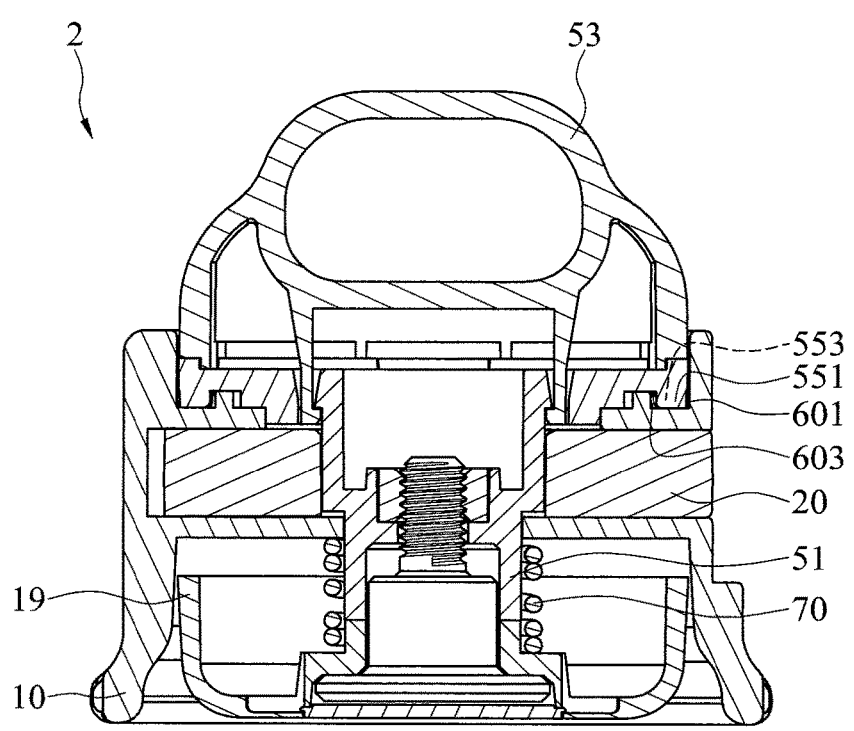
FIG. 8 illustrates a cross-sectional view of the second embodiment of the oral dilator showing a positioning member at a lock state.
Figure 9:
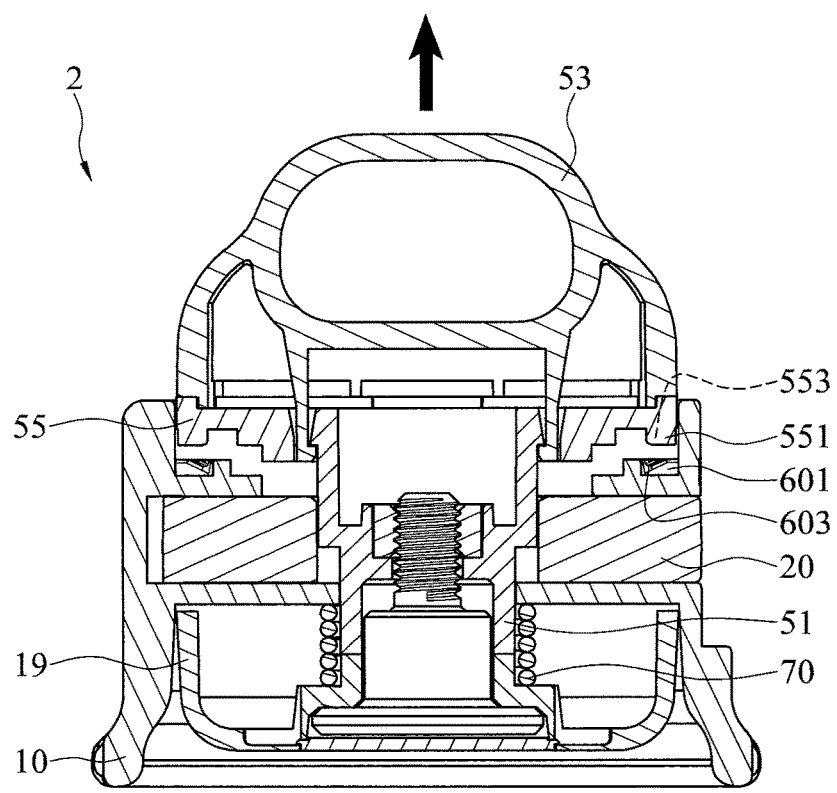
FIG. 9 illustrates another cross-sectional view of the second embodiment of the oral dilator showing the positioning member at an unlock state.

FIG. 8 illustrates respectively a cross-sectional view of the second embodiment of the oral dilator showing the positioning member at a lock state. FIG. 9 illustrates another cross-sectional view of the second embodiment of the oral dilator showing the positioning member at an unlock state. As shown in FIG. 8, when the crests of the first teeth portion 551 of the rotary portion 55 are located at the valleys 603 of the second teeth portion 601, the spring 70 is at normal state (not pressed). As shown in FIG. 9, when the first teeth portion 551 is pulled away by a user or patient from the second teeth portion 601, the spring 70 is pressed and an internal elastic force is formed. The elastic force pushes the first teeth portion 551 toward the second teeth portion 601. As shown in FIG. 9, the first and second teeth portion 551, 601 are not engaged with each other, the rotary portion 55 can be rotated (the positioning member is at an unlock state). After the user adjusts the dilation angle to a desired angle, the user may release the rotary switch 53. Then, the elastic force of the spring 70 pushes the first teeth portion 551 toward the second teeth portion 601 and makes them engaged with each other to fixed the first and second duckbilled element 13, 23 at the desired angle. That is, when the first teeth portion 551 is engaged with the second teeth portion 601, the rotary switch 53 is locked (stopped from being rotated) and a dilation angle between a first duckbilled element 13 and a second duckbilled element 23 is fixed, as shown in FIG. 8.

In addition, the peripheral wall 111 is engraved with graduations 1117 at two sides of the inserting groove 117.

The graduations 1117 correspond to rotated angles of the rotary portion 55 and dilation angles between the second duckbilled element 23 and the first duckbilled element 13, as reference for recordation of rehabilitation.

According to the content disclosed in the foregoing embodiments, a structure of an oral dilator is ergonomic. A patient can operate the oral dilator without help from others. Moreover, a dilation angle between the duckbilled elements of the dilator can be determined and slightly adjusted by the patient, thereby benefiting gradual mouth-opening rehabilitation and avoiding causing a painful feeling caused by excessive dilation. It is convenient to observe rehabilitation situations, which facilitates use of a patient and further encourages the patient, thereby avoiding fibrosis of chewing tissues, and improving food-taking and life quality of the patient.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. An oral dilator, comprising:
   a first body comprising a housing and a first duckbilled element, wherein the first duckbilled element is extended from the housing;
   a second body comprising a connecting portion and a second duckbilled element, wherein the connecting portion is assembled with the housing, the second duckbilled element is extended from the connecting portion, and the second duckbilled element is moved away from or toward the first duckbilled element for operating the oral dilator open or close;
   a rotary member comprising a central shaft, and a gearwheel element, wherein the gearwheel element includes a unidirectional gear row, the central shaft penetrates through the first body and the second body and connects to the gearwheel element, and the rotary member drives to rotate the second body, and the second duckbilled element is moved for operating the oral dilator open or close;
   a positioning member disposed on the first body and comprising a toggle block and a ratchet gear row, wherein the toggle block controls an engagement of the ratchet gear row and the unidirectional gear row, and the rotary member is only rotated along a single direction while the ratchet gear row engages with the unidirectional gear row.

2. The oral dilator according to claim 1, wherein the housing comprises a peripheral wall and an upper cover, the upper cover is above the second body, the rotary member, and the positioning member, the periphery wall is connected to the upper cover and forms an accommodation space therebetween, the peripheral wall is provided with an inserting groove which communicates to the accommodation space, the upper cover is provided with a first opening, the connecting portion is provided with a second opening, and the connecting portion of the second body is inserted into the inserting groove.

3. The oral dilator according to claim 2, wherein the positioning member further comprises a spring and a driving lever, the spring abuts against the ratchet gear row and an inner surface of the peripheral wall, the driving lever is extended out from a surface of the toggle block, when the driving lever is driven by power, the toggle block and the ratchet gear row are driven to move, and the spring is pressed, so that the unidirectional gear row is not in contact with the ratchet gear row, and when force on the driving lever is removed, an elastic force of the spring drives the toggle block and the ratchet gear row to be restored, so that the ratchet gear row engages with the unidirectional gear row.

4. The oral dilator according to claim 3, wherein the first body further comprises a bottom cover, the bottom cover is under the peripheral wall, the upper cover, the second body, the rotary member, and the positioning member, and the bottom cover is fastened to at least one connection member extended from the lower surface of the upper cover, and seals the accommodation space, the bottom cover is provided with a sliding groove, and the driving lever passes through the sliding groove and protrudes above the bottom cover.

5. The oral dilator according to claim 2, wherein the gearwheel element is provided with a third opening, the central shaft passes through the first opening, the second opening, and a third opening.

6. The oral dilator according to claim 5, further comprising a fastening bolt, wherein the first opening of the first body is provided with a first groove, the second opening of the connecting portion is provided with a second groove, the third opening is provided with a third groove, the first groove, the second groove, and the third groove are in communication, the fastening bolt is fastened to the first groove, the second groove, and the third groove and abuts against the central shaft.

7. The oral dilator according to claim 2, wherein the rotary member further comprises a rotary switch, wherein the rotary switch is at an upper surface of the upper cover, and two ends of the central shaft are connected to the rotary switch and the gearwheel element, respectively.

8. The oral dilator according to claim 1, wherein the toggle block comprises a first through-hole, the ratchet gear row comprises a second through-hole, and the toggle block is pivotally connected to the ratchet gear row by using a latch passing through the first through-hole and the second through-hole.

9. The oral dilator according to claim 1, further comprising a snap ring, wherein the snap ring is in contact with a surface of the gearwheel element, and one end of the central shaft is sleeved by the snap ring.

10. The oral dilator according to claim 1, wherein the inserting groove is engraved with multiple graduations, and the graduations correspond to intersection angles between the first duckbilled element and the second duckbilled element.

11. An oral dilator, comprising:
    a first body comprising a housing and a first duckbilled element, wherein the housing comprises a peripheral wall and an upper cover, the periphery wall is connected to the upper cover and forms an accommodation space therebetween, the peripheral wall is provided with an inserting groove which communicates with the accommodation space, the upper cover is provided with a first opening, and the first duckbilled element is extended from the housing;
    a second body comprising a connecting portion and a second duckbilled element, wherein the connecting portion is inserted into the inserting groove, the connecting portion is provided with a second opening, and the second duckbilled element is extended from the connecting portion and corresponding to the first duckbilled element;

a rotary member comprising a central shaft, a rotary switch and a rotary portion, wherein the central shaft passes through the first opening and the second opening, the central shaft is connected to the rotary portion, the rotary portion is between the rotary switch and an upper surface of the upper cover, the rotary portion is provided with a first teeth portion, and the rotary member is capable of being rotated to drive the second body to rotate;

a positioning member comprising a second teeth portion disposed on a surface of the upper cover of the first body, and the rotary member is locked when the second teeth portion engages with the first teeth portion, wherein the upper cover is above the second body, the rotary member, and the positioning member.

12. The oral dilator according to claim 11, further comprising a spring, wherein the spring is located in the accommodation space, the central shaft is sleeved by the spring, the spring is in contact with a lower surface of the upper cover, the spring is not pressed when the first teeth portion engages with the second teeth portion, and when the first teeth portion is moved away from the second teeth portion, an elastic force of the spring is formed to push the first teeth portion toward the second teeth portion.

13. The oral dilator according to claim 12 further comprising a fastening component, wherein the fastening component is located in the accommodation space and sleeved by the spring, and the fastening component fastens the central shaft.

14. The oral dilator according to claim 13, wherein the first body further comprises a bottom cover, the bottom cover comprises a fastening groove to receive the fastening component, and the bottom cover and the peripheral wall are connected to seal the accommodation space.

15. The oral dilator according to claim 13, wherein the fastening component comprises a screw and a nut, the nut is located at a central groove area of the rotary member, and corresponds to the first opening, the screw passes through the central shaft and buckles with the nut.

16. The oral dilator according to claim 15, wherein a diameter of the head of the screw is greater than a diameter of the central shaft.

17. The oral dilator according to claim 11, wherein the rotary portion and the central shaft are integrally formed, and the rotary portion is formed by extending in a loop at an outer surface of one end of the central shaft.

18. The oral dilator according to claim 11, wherein the inserting groove is engraved with a plurality of graduations, and the graduations correspond to dilation angles between the first duckbilled element and the second duckbilled element.

* * * * *